(12) United States Patent
Johansson

(10) Patent No.: US 11,040,185 B2
(45) Date of Patent: Jun. 22, 2021

(54) DISPOSABLE TATTOO NEEDLE CARTRIDGE

(71) Applicant: Ink Machines Sweden AB, Växjö (SE)

(72) Inventor: Christian Johansson, Växjö (SE)

(73) Assignee: Ink Machines Sweden AB, Växjö (SE)

( * ) Notice: Subject to any disclaimer, the term of this patent is extended or adjusted under 35 U.S.C. 154(b) by 110 days.

(21) Appl. No.: 16/093,668

(22) PCT Filed: Apr. 15, 2016

(86) PCT No.: PCT/EP2016/058411
§ 371 (c)(1),
(2) Date: Oct. 15, 2018

(87) PCT Pub. No.: WO2017/178069
PCT Pub. Date: Oct. 19, 2017

(65) Prior Publication Data
US 2019/0134371 A1 May 9, 2019

(51) Int. Cl.
*A61M 37/00* (2006.01)
(52) U.S. Cl.
CPC ... *A61M 37/0076* (2013.01); *A61M 2205/106* (2013.01)
(58) Field of Classification Search
CPC ........ A61M 37/0076; A61M 2205/106; A61M 2205/10; A61M 2205/33; A61M 37/0015; A61M 2037/0023; A61M 37/0084; A61M 2037/003; A61F 9/0076; A61B 5/150984;
(Continued)

(56) References Cited

U.S. PATENT DOCUMENTS 3,702,940 A    11/1972  Stewart
4,900,252 A     2/1990  Liefke et al.
(Continued)

FOREIGN PATENT DOCUMENTS

CN     204502099 U    7/2015
DE      29919199 U1   1/2000
(Continued)

OTHER PUBLICATIONS

International Search Report and Written Opinion for PCT/EP2016/058412 dated Feb. 16, 2017, 11 pages.
(Continued)

*Primary Examiner* — Katherine M Shi
(74) *Attorney, Agent, or Firm* — Brundidge & Stanger, P.C.

(57) ABSTRACT

A disposable tattoo needle cartridge (14) for connecting to a tattoo machine drive unit comprises a cartridge housing (26) and a needle assembly (28) comprising a needle driver connector (36) and at least one needle (16), the needle driver connector (36) being connectable to a needle driver (38) of the tattoo machine drive unit (12) for receiving a reciprocating motion, the needle assembly (28) being slidingly arranged in the tattoo needle cartridge (26) to allow said reciprocating motion along a reciprocation axis (A), wherein the cartridge housing (26) has a front end portion provided with a needle nozzle for allowing the at least one needle (16) to reciprocatingly protrude from the tattoo needle cartridge (14); and a rear end portion (30) configured to be connected to the tattoo machine drive unit (12), wherein the needle driver connector (36) comprises a needle assembly magnet (44) for connecting to a mating drive magnet (46) of the needle driver (38) in a contact-less manner in a radial, with respect to the reciprocation axis (A), connection direction.

11 Claims, 4 Drawing Sheets

(58) Field of Classification Search
CPC .......... A61B 2017/00747; A61B 2017/00761; A61B 17/32002; A01K 11/005
See application file for complete search history.

(56) References Cited

U.S. PATENT DOCUMENTS

| | | |
|---|---|---|
| 5,873,717 A | 2/1999 | Behringer |
| D613,572 S | 4/2010 | Nielsen |
| 7,969,715 B2 | 6/2011 | Copeland |
| 8,228,666 B2 | 7/2012 | Rickard |
| 10,220,196 B2 | 3/2019 | Johansson |
| 10,449,346 B2 | 10/2019 | Juan |
| 2002/0069726 A1 | 6/2002 | Adler et al. |
| 2005/0010236 A1 | 1/2005 | Frister |
| 2006/0020283 A1 | 1/2006 | Lisec |
| 2008/0254404 A1 | 10/2008 | Heraud |
| 2010/0036317 A1 | 2/2010 | Oginski et al. |
| 2010/0241151 A1 | 9/2010 | Rickard |
| 2012/0199150 A1 | 8/2012 | Le |
| 2013/0123825 A1 | 5/2013 | Demjanenko |
| 2013/0226211 A1 | 8/2013 | Xiao |
| 2015/0025561 A1 | 1/2015 | La Fontaine |
| 2015/0202420 A1 | 7/2015 | Miller et al. |
| 2016/0074057 A1* | 3/2016 | Jezierski .......... A61B 17/32002 606/171 |
| 2016/0354592 A1 | 12/2016 | Juan |
| 2017/0021154 A1 | 1/2017 | Johansson |
| 2018/0028799 A1 | 2/2018 | Hofung |
| 2019/0134371 A1 | 5/2019 | Johansson |
| 2019/0134372 A1 | 5/2019 | Johansson |
| 2020/0086103 A1 | 3/2020 | Juan |

FOREIGN PATENT DOCUMENTS

| | | |
|---|---|---|
| DE | 102011120366 A1 | 6/2013 |
| EP | 2826518 A1 | 1/2015 |
| GB | 2488323 A | 8/2012 |

OTHER PUBLICATIONS

International Search Report and Written Opinion for PCT/EP2016/058411 dated Mar. 21, 2017, 17 pages.
2nd Office Action from CN Application No. 2016800845838 dated Mar. 23, 2021.

* cited by examiner

Fig. 1a
Fig. 1b
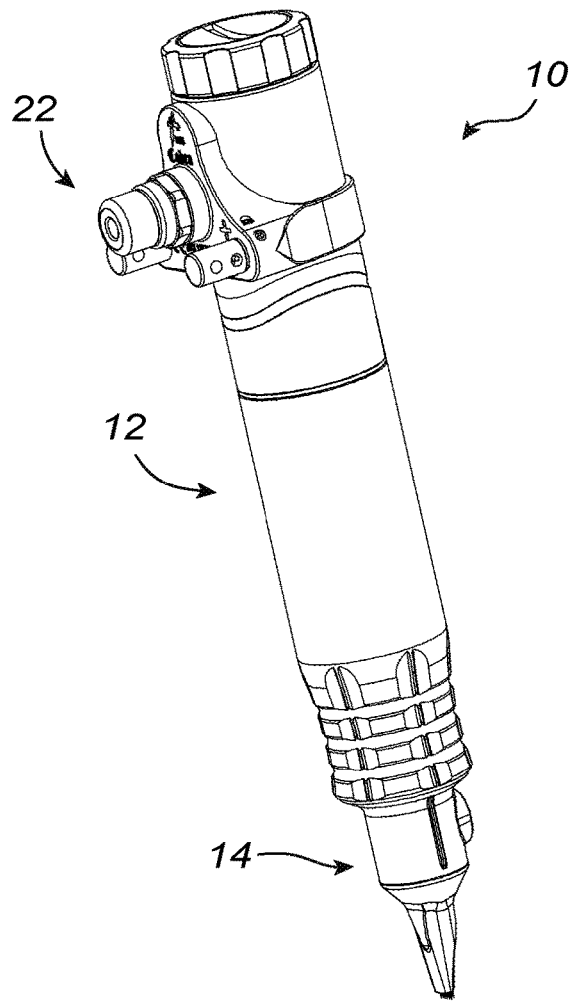
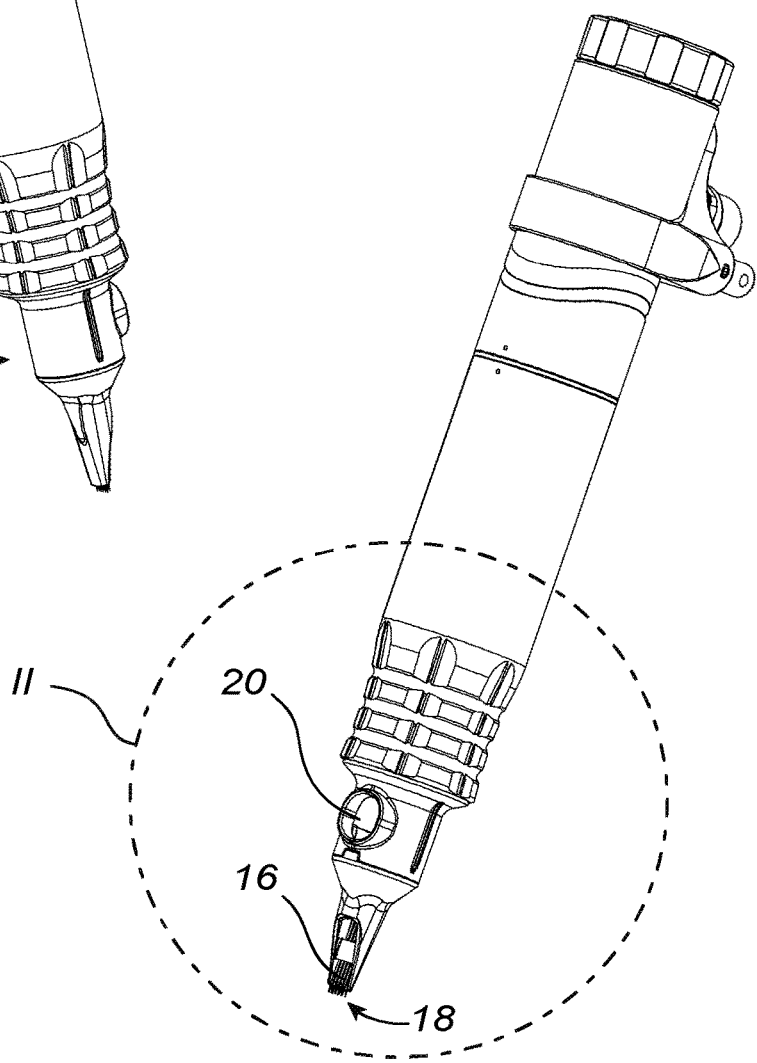

DISPOSABLE TATTOO NEEDLE CARTRIDGE

CROSS-REFERENCE TO RELATED APPLICATION

This Application is the National Stage filing under 35 U.S.C. § 371 of PCT Application Ser. No. PCT/EP2016/058411 filed on Apr. 15, 2016, the disclosure of which is hereby incorporated herein by reference in its entirety.

FIELD OF THE INVENTION

The present invention relates to a disposable tattoo needle cartridge, a method of producing a disposable tattoo needle cartridge, a method of inserting a disposable tattoo needle cartridge into a tattoo machine drive unit, a tattoo machine drive unit for a disposable tattoo needle cartridge, a needle driver for driving the needle of a disposable tattoo needle cartridge, and a method of operating a tattoo machine.

BACKGROUND OF THE INVENTION

DE 10 2011 120 366 A1 describes an exemplary tattoo machine. Creating tattoo art may be time consuming and physically exhausting, as the ink is permanent and needs to be delivered at the correct location with a high level of accuracy. Differently shaped needles may be used for different parts of the artwork. For hygiene reasons, the tattooing machine is typically covered in a disposable plastic bag when creating body artwork. Obviously, the tattooing equipment faces many different requirements ranging across cost efficiency, ergonomics, versatility and flexibility, efficiency, reliability, precision, and hygiene. There is an incessant strive to provide improved tattooing equipment that renders the tattooing process more safe, efficient, reliable and convenient.

SUMMARY OF THE INVENTION

It is an object of the present invention to solve, or at least mitigate, parts or all of the above mentioned problems. To this end, there is provided a disposable tattoo needle cartridge for connecting to a tattoo machine drive unit, the tattoo needle cartridge comprising a cartridge housing and a needle assembly comprising a needle driver connector and at least one needle, the needle driver connector being connectable to a needle driver of the tattoo machine drive unit for receiving a reciprocating motion, the needle assembly being slidingly arranged in the tattoo needle cartridge to allow said reciprocating motion along a reciprocation axis, wherein the cartridge housing has a front end portion provided with a needle nozzle for allowing the at least one needle to reciprocatingly protrude from the tattoo needle cartridge; and a rear end portion configured to be connected to the tattoo machine drive unit, wherein the needle driver connector comprises a needle assembly magnet for connecting to a mating drive magnet of the needle driver in a contact-less manner in a radial, with respect to the reciprocation axis, connection direction. The magnetic engagement between a needle assembly magnet and a drive magnet allows for a well-defined and distinct position of equilibrium in the positional relation between the needle assembly and the drive magnet. Thereby, the reciprocating motion of the needle assembly will be well-defined and controlled.

According to an embodiment, the needle cartridge comprises a releasable needle assembly retainer for retaining the needle assembly at a retracted retain position in which the at least one needle does not protrude from the needle nozzle, wherein the needle assembly upon release of said needle assembly retainer is movable from the retracted retain position to an advanced operating position at which the needle is free to reciprocate without engaging with the needle assembly retainer. Such a retainer provides a safety arrangement, allowing completely safe handling of the cartridge before connecting it to the drive unit.

According to an embodiment, the needle assembly retainer is self-contained in the tattoo needle cartridge. The term self-contained should be construed as the entire retainer forming part of the cartridge in a non-removable manner, which facilitates re-activation of the retainer e.g. when removing the cartridge.

According to an embodiment, the needle assembly retainer is configured to automatically release when a force acting upon the needle assembly towards the needle nozzle exceeds a limit force. Such a configuration enables a very simple release of the retainer, e.g. when connecting the cartridge to the drive unit. By way of example, the retainer may be formed by a friction engagement and/or a magnetic engagement between the needle assembly and a portion of the cartridge housing.

According to an embodiment, the needle assembly retainer is configured to automatically engage with the needle assembly when the needle assembly reaches a retracted retain position. Such a position may typically be reached when needle is removed from/pulled out of the drive unit.

According to an embodiment, the needle assembly retainer comprises a ferromagnetic element for holding the needle assembly magnet in the retracted position. Such a retainer is simple and requires very few parts. By way of example, the ferromagnetic element may be configured as a washer located at, or forming, a back wall of the cartridge housing.

According to an embodiment, the needle assembly magnet has a magnetic moment aligned in a first direction essentially parallel with the reciprocation axis. Such a cartridge is particularly well suited to be driven by a drive magnet having a magnetic moment aligned in a second direction which is essentially opposite to the first direction, such as a ring magnet having an axial polarity. Moreover, such a design will make the axial connection between the magnets particularly strong, and provide a more distinct axial position, due to the more highly progressive or non-linear force required to axially separate the magnets once engaged. A needle assembly retainer may facilitate preventing the at least one needle from being pushed out of the needle cartridge when connecting the cartridge to the drive unit. It is acknowledged that from a strictly physical perspective, a magnet may consist of atoms or microscopic regions of opposing magnetic moments, which together sum up to a macroscopic magnetic moment. However, throughout this disclosure, the term "magnetic moment" of a magnet refers to the macroscopic phenomenon only, i.e. for an aggregate, integrated magnetic moment, corresponding to an overall magnetic polarity of the magnet.

According to an embodiment, the rear end portion of the cartridge housing is provided with at least one inner spacer element, introducing a radial gap between the needle assembly magnet and an inner wall surface of the rear end portion of the cartridge housing, for defining an air escape passage between a rear space behind the needle assembly magnet and a front space in front of the needle assembly magnet. By allowing air to pass relatively freely between the front and rear spaces, the motion of the needle assembly will not be considerably impaired by air pressure built up on either side of the needle assembly magnet when the needle assembly moves at high speed. The spacer element may also provide radial stability to the needle assembly. By way of example, the spacer may be configured as one or several internal ridges protruding radially inwards from the cartridge housing and extending along the reciprocation axis. The ridges may be integrally formed with the cartridge housing. Preferably, the ridges are essentially straight, and/or are essentially parallel with the reciprocation axis.

According to an embodiment, the rear end portion of the cartridge housing is provided with at least one outer spacer element for introducing a radial gap between an outer wall surface of the rear end portion of the cartridge housing and the drive magnet. By allowing air to pass freely between the front and rear side spaces of the drive magnet, the motion of the drive magnet will not be considerably impaired by air pressure built up on either side of the drive magnet when the drive magnet moves at high speed. This may be particularly desirable in combination with a ring-shaped drive magnet. By way of example, the spacer may be configured as one or several external ridges protruding radially outwards from the cartridge housing and extending along the reciprocation axis. The ridges may be integrally formed with the cartridge housing. Preferably, the ridges are essentially straight, and/or are essentially parallel with the reciprocation axis.

According to an embodiment, the rear end portion of the cartridge housing is sealed by a rigid wall. Such a design is hygienic, since it prevents body fluids from being transported to the tattoo machine drive unit, and exposes no external moving parts to the tattoo machine drive unit. A rigid wall may also prevent the needle from being pulled out of the cartridge by the engagement with the drive magnet when the cartridge is removed from the tattoo machine drive unit.

According to an embodiment, the needle assembly is freely slidable along the reciprocation axis in a non-resilient manner. Such a design reduces the drive power required from the tattoo machine drive unit, which reduces vibrations and extends battery life as the case may be.

According to an embodiment, a rear end of the needle driver connector comprises a radially extending ferromagnetic flange and a needle assembly magnet alignment structure extending rearwards from the ferromagnetic flange. Such a design facilitates the assembly of the cartridge, since the needle assembly magnet may simply be placed on, and thereby magnetically snap to, the ferromagnetic flange. The alignment structure will maintain the magnet radially aligned on the rear end of the needle driver connector. By way of example, the alignment structure may comprise an alignment pin onto which, e.g., a magnet provided with a mating hole may be slipped.

According to another aspect, parts, or all, of the above mentioned problems are solved, or at least mitigated, by a method of producing a disposable tattoo needle cartridge, the method comprising providing a needle driver connector comprising a radially extending ferromagnetic flange and a needle assembly magnet alignment structure extending from the ferromagnetic flange; providing a needle assembly magnet comprising an alignment structure configured to mate with the alignment structure extending from the ferromagnetic flange; and placing the needle assembly magnet onto the ferromagnetic flange such that the alignment structure of the needle assembly magnet mates with the alignment structure of the ferromagnetic flange. Such a way of attaching the magnet is fast, easy and requires no chemicals.

According to yet another aspect, parts, or all, of the above mentioned problems are solved, or at least mitigated, by a tattoo machine drive unit for driving the needle assembly of a disposable tattoo needle cartridge as defined hereinbefore, the tattoo machine drive unit comprising a needle cartridge socket for receiving the disposable tattoo needle cartridge; a needle driver for driving the needle assembly of the disposable tattoo needle cartridge in a reciprocating motion along a reciprocation axis, the needle driver being configured to axially reciprocate along said reciprocation axis and comprising a ring-shaped drive magnet enclosing the needle cartridge socket, the drive magnet having a magnetic moment aligned in a first direction essentially parallel with the reciprocation axis and being connectable to a mating needle assembly magnet of the needle assembly in a contact-less manner in a radial, with respect to the reciprocation axis, connection direction, the needle assembly magnet having a magnetic moment aligned in a second direction essentially opposite to the first direction. Such a drive unit may be used for driving a needle cartridge as described hereinbefore.

According to still another aspect, parts, or all, of the above mentioned problems are solved, or at least mitigated, by a needle driver for driving the needle assembly of a disposable tattoo needle cartridge in a reciprocating motion along a reciprocation axis, the needle driver comprising a ring-shaped drive magnet having a magnetic moment aligned in a first direction essentially parallel with the reciprocation axis and being connectable to a mating needle assembly magnet of the needle assembly in a contact-less manner in a radial, with respect to the reciprocation axis, connection direction, the needle assembly magnet having a magnetic moment aligned in a second direction essentially opposite to the first direction, the needle driver further comprising a second, driven magnet for connecting to a drive piston of a tattoo machine drive unit. Such a needle driver can easily be removed and replaced by an operator, since it can be connected to the drive piston via a magnetic interface. The user can thereby easily and quickly switch between needle drivers having different magnetic properties of their respective drive magnets, such that different levels of resilience may be obtained in the engagement between the drive magnet and the needle assembly magnet.

According to still another aspect, parts, or all, of the above mentioned problems are solved, or at least mitigated, by a method of inserting a disposable tattoo needle cartridge in a tattoo machine drive unit, the method comprising inserting a rear end portion of the cartridge in a needle cartridge socket of the tattoo machine drive unit, thereby bringing a needle assembly of the tattoo needle cartridge into engagement with a needle driver of the tattoo machine drive unit; and inserting the rear end portion of the cartridge deeper into the needle cartridge socket of the tattoo machine drive unit, thereby releasing the needle assembly from a needle assembly retainer holding the needle assembly in a retracted position. Such a method provides a very simple, efficient and safe way of handling needle cartridges.

According to still another aspect, parts, or all, of the above mentioned problems are solved, or at least mitigated, by a method of operating a tattoo machine, the method comprising reciprocating a tattoo needle along a reciprocation axis via a radial, with respect to said reciprocation axis, and contact-less magnetic engagement between a drive magnet and a needle assembly magnet.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings, where the same reference numerals will be used for similar elements, wherein:

FIG. 1a is a diagrammatic view from a first perspective of a tattoo machine;

FIG. 1b is a diagrammatic view from a second perspective of the tattoo machine of FIG. 1a;

FIG. 6b is a perspective view of a section of the needle driver of FIG. 6a;

DETAILED DESCRIPTION OF THE EXEMPLARY EMBODIMENTS

Figure 2:
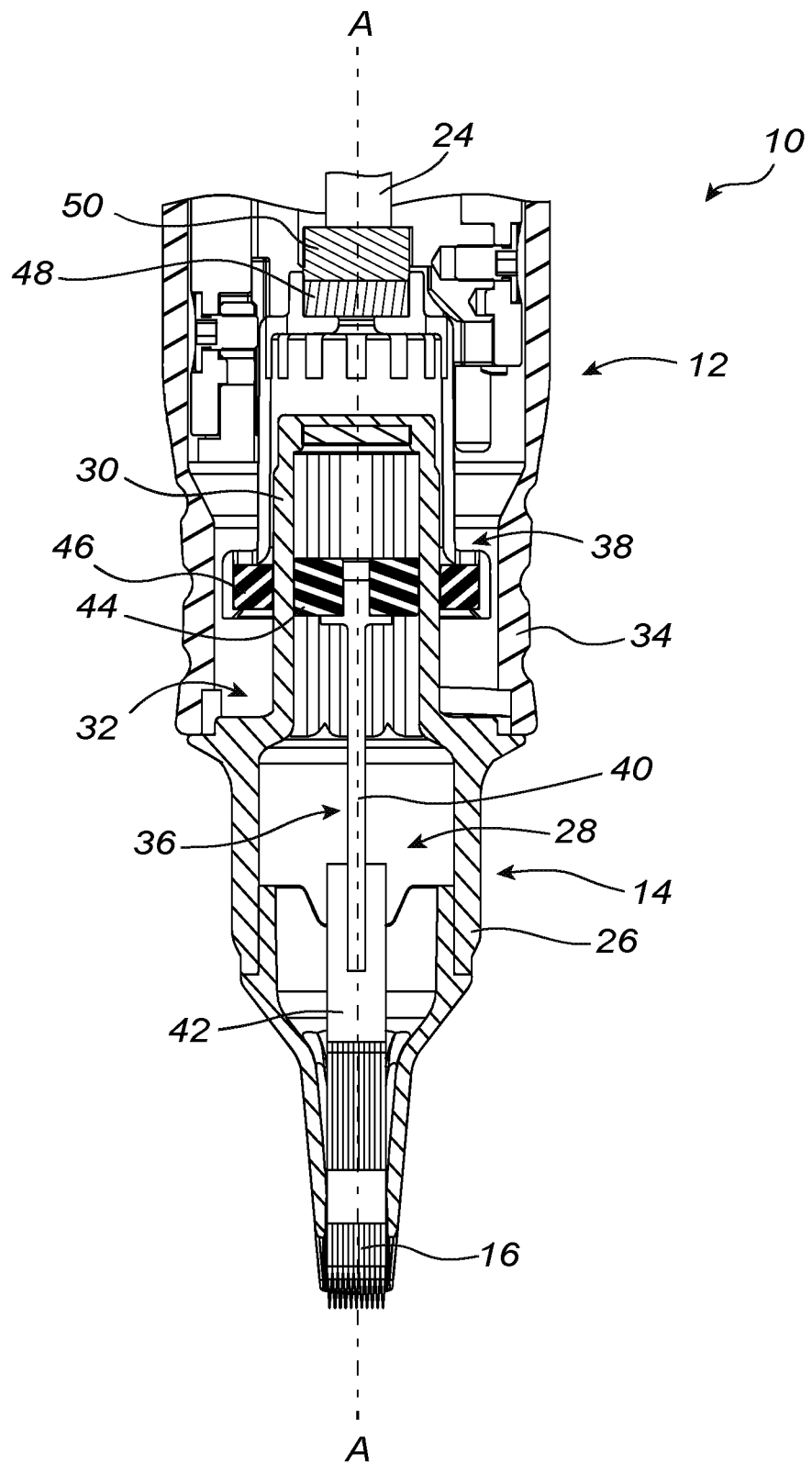
FIG. 2 illustrates a longitudinal section of a lower portion the tattoo machine of FIGS. 1a-b as indicated by a dashed circle in FIG. 1b.

FIGS. 1a-b illustrate, from two different perspectives, an exemplary tattoo machine 10 comprising a drive unit 12 and a tattoo needle cartridge 14. The tattoo needle cartridge 14 is disposable, i.e., it is intended for use during a single tattooing session on one single subject person only, and then discarded for hygiene reasons. Preferably, it is also sterile at the start of a tattooing session; sterilization may typically be performed during production of the cartridge 14. The tattoo machine 10, which has the general shape of a pen, is configured to reciprocate a needle assembly provided with a set of needles 16 protruding from a needle nozzle 18 at a lower end of the tattoo machine. The needle cartridge 14 is provided with an opening 20 for receiving ink to be delivered into the skin of a subject person to be tattooed by the reciprocating needles 16. The drive unit 12 is provided with an electrical interface 22 for receiving an electric drive current from a tattoo machine controller (not shown), and comprises an electric motor (not shown) and a conversion mechanism (not shown) for converting a rotary motion of the electric motor to an axially reciprocating motion of a piston. Such functions and features of tattoo machine drive units are known in the art, and will not be described in greater detail here.

FIG. 2 illustrates a longitudinal section of a lower portion of the tattoo machine 10 indicated by a dashed circle II in FIG. 1b. A piston 24, driven by the electric motor and conversion mechanism, is configured to oscillate or reciprocate along a reciprocation axis A, and thereby reciprocate the needles along said axis A. The needle cartridge 14 comprises a housing 26, in which a needle assembly 28 comprising the needles 16 is slidingly arranged to allow said reciprocating motion along the reciprocation axis A. A rear end 30 of the cartridge housing 26 is inserted into a needle cartridge socket 32 of the drive unit 12, and the cartridge housing 26 is removably and firmly attached to an outer housing 34 of the drive unit 12.

In addition to the needles 16, the needle assembly 28 also comprises a needle driver connector 36 for connecting the needles 16 to a needle driver 38 of the tattoo machine drive unit 12. The needle driver connector 36 comprises a pin 40 soldered to an attachment plate 42, onto which the needles 16 are soldered, and a needle assembly magnet 44 for magnetically connecting to a mating drive magnet 46 of the needle driver 38 in a radial, with respect to the reciprocation axis A, connection direction. The magnetic connection is contact-less and based on the magnetic engagement between the needle assembly magnet 44 and the drive magnet 46 through the wall of the rear end 30 of the cartridge housing 26. The needle assembly magnet 44 and the drive magnet 46 are both polarized along the reciprocation axis, but in opposite directions, i.e. assuming that the needle assembly magnet 44 has its north pole facing upwards, towards the piston 24, the drive magnet 46 has its north pole facing downwards, towards the needles 16. The radial engagement between the drive magnet 46 and the needle assembly magnet 44 allows the entire rear end portion 30 of the cartridge housing 26 to be integrally formed, rigid, and hermetically sealed, completely eliminating the risk of any leakage of biologic material in this direction due to untightness or malfunctioning of any moving or flexible parts.

FIG. 2 illustrates the two magnets 44, 46 in a stable position of equilibrium relative to each other, wherein the north pole of the needle assembly magnet 44 is vertically aligned with the south pole of the drive magnet 46 and vice versa. Even the slightest deviation from this position will create a strong returning force towards the illustrated stable position; hence, the use of two mating magnets for the engagement between needle driver 38 and needle driver connector 36 provides a well-defined and distinct position of equilibrium in the positional relationship between the needle assembly magnet 44 and the drive magnet 46. In the illustrated embodiment, the needle assembly magnet 44 has a circular cylindrical outer mantle surface, and the drive magnet 46 is a ring magnet having an inner circular cylindrical surface enclosing the needle assembly magnet 44.

The drive magnet 46 of the needle driver 38 defines a lower, drive interface towards the cartridge 14. The needle driver 38 is also provided with a second, driven magnet 48 defining an upper, driven interface towards the drive piston 24. For the purpose, the piston 24 is provided with a drive magnet 50, attracting the driven magnet 48 to bring it into direct, physical engagement or abutment. The magnetic interface allows for very easy removal of the needle driver 38 from the drive unit 12. Moreover, the axial, physical contact between the needle driver 38 and the piston 24 provides a very well-defined motion of the needle driver 38 relative to the motion of the piston 24. As an alternative to having two mating magnets in the interface between the needle driver 38 and the piston 24, either of the magnets 48, 50 might be just a ferromagnetic component without an aggregate magnetic moment.

Figure 3:
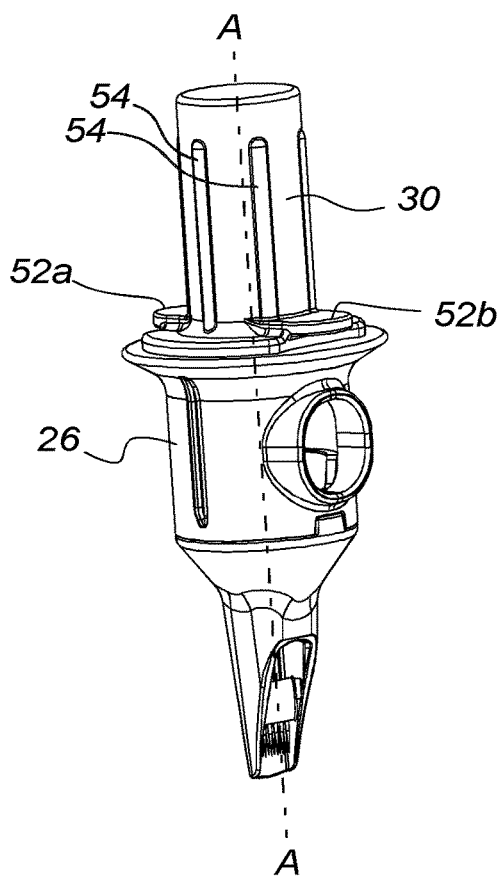
FIG. 3 is a diagrammatic view in perspective of a disposable tattoo machine cartridge.

Turning now to FIG. 3, the rear end portion 30 of the needle cartridge housing 26 defines a cylinder of circular-cylindrical cross-section, allowing the needle assembly magnet 44 (cf. FIG. 2) to move axially along the length thereof. A pair of bayonet wings 52a-b define a first part of a bayonet joint, for connecting to a second part (not shown) of said bayonet joint provided in the needle cartridge socket 32 (cf. FIG. 2) of the drive unit 12 to allow firmly attaching the cartridge 14 to the drive unit 12. External ridges 54 protrude radially outwards from, and are distributed about the periphery of, the outer surface of the needle cartridge housing's end portion 30. The ridges 54 extend parallel to the reciprocation axis A, and guide the drive magnet 46 along its path along the axis A.

Figure 4:
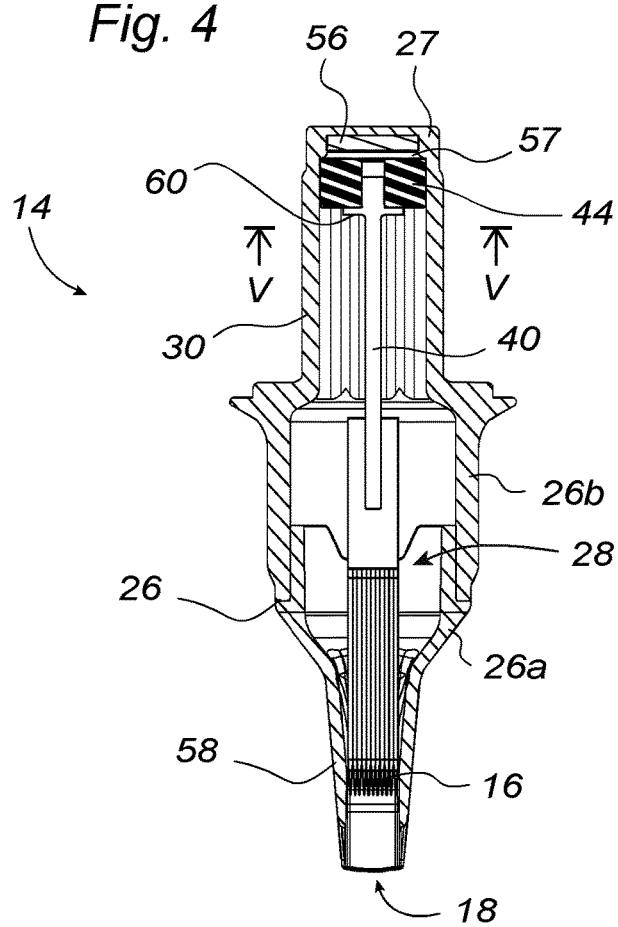
FIG. 4 is a longitudinal section of the disposable tattoo machine cartridge of FIG. 3.

The cross-section of FIG. 4 illustrates the cartridge in greater detail, and when in a state taken when not inserted in a tattoo machine drive unit 12 (cf. FIG. 1). A ferromagnetic washer 56, which may be made of e.g. iron or steel, is fixed at a rearmost position inside the rear end portion 30 of the needle cartridge housing 26. The washer 56 holds the needle assembly 28 in a retracted retain position, keeping the sharp pin ends of the needles 16 protected inside a front end portion 58 of the needle cartridge housing 26, until the cartridge 14 is inserted in the needle cartridge socket 32 of the drive unit 12 (cf. FIG. 2). FIG. 4 also illustrates an air gap 57 between the needle assembly magnet 44 and the ferromagnetic washer 56. The gap is not necessary, but merely provides a means of fine-tuning the attraction force between the needle assembly magnet 44 and the ferromagnetic washer 56, the purpose of which will be elucidated further below. Alternatively, the gap may be filled with a non-ferromagnetic material; by way of example, it may be formed by plastic, and it may also be integral with the needle cartridge housing 26. The needle cartridge housing 26 is formed by a foremost housing piece 26a and a rearmost housing piece 26b, allowing the needle assembly to be inserted into the cartridge 14 when assembling the cartridge 14. The housing 26 has a rigid back wall portion 27, which defines a rearwardmost stop position for the needle assembly 28. The needle assembly magnet 44 is attached to the pin 40, which is of a ferromagnetic material such as ferromagnetic steel, by magnetic attraction only, which facilitates assembly. The housing 26 may be made of e.g. polyoxymethylene, i.e., acetal plastic, which provides a high level of durability as well as low friction.

A ferromagnetic collar or flange 60 provides axial support for the magnet 44, and the rearmost portion of the pin 40 extending behind the flange 60 provides radial alignment and support.

Figure 5:
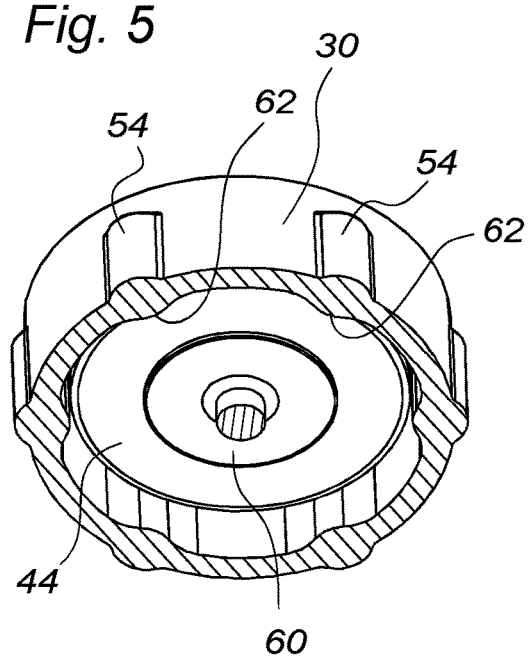
FIG. 5 is a section of the disposable tattoo machine cartridge of FIGS. 3-4, as taken along V-V of FIG. 4.

FIG. 5 is a perspective view of the needle cartridge 14 as seen in a section taken along V-V of FIG. 4. Internal ridges 62 protrude radially inwards from, and are distributed about the periphery of, the inner surface of the needle cartridge housing's end portion 30. The ridges 62 extend parallel to the reciprocation axis A (cf. FIG. 5), and guide the needle assembly magnet 44 along its path along the axis A.

Figure 6A:
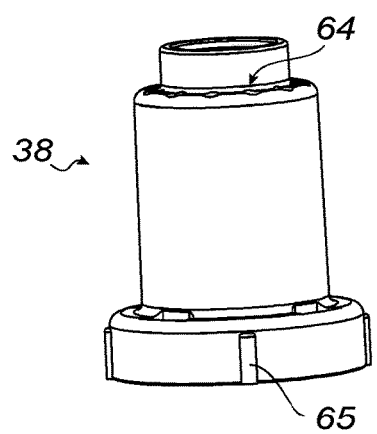
FIG. 6a is a diagrammatic view in perspective of a needle driver for the tattoo machine of FIGS. 1a-b and 2.

FIG. 6a illustrates the needle driver 38 in greater detail. Air escape holes 64 allow air to pass between the space defined by the needle driver 38 and the rear end portion 30 of the cartridge housing 26 (FIG. 2), and a space behind the needle driver. External ridges 65 protrude radially outwards from, and are distributed about the periphery of, the outer surface of the needle driver 38. The ridges 65 extend parallel to the reciprocation axis A (cf. FIG. 3), and provide radial support for guiding the needle driver 38 along its path parallel to the axis A.

Figure 6B:
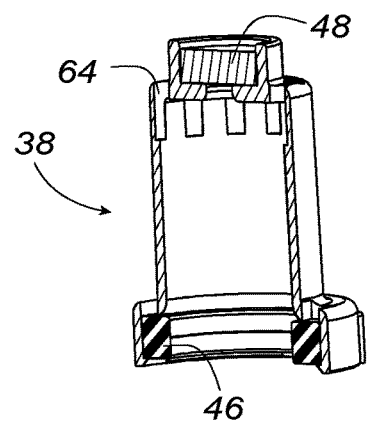

FIG. 6b illustrates a section of the needle driver 38, showing the ring-shaped drive magnet 46 and the driven magnet 48, as well as the air holes 64.

Figure 7A:
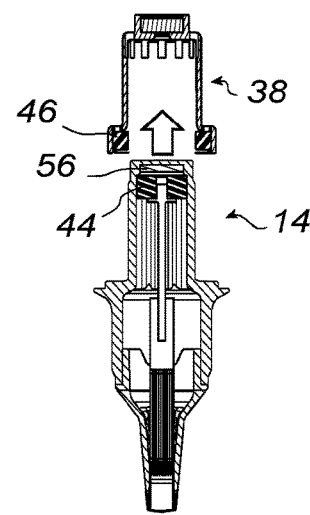
FIG. 7a is a longitudinal section illustrating the insertion of the disposable tattoo needle cartridge of FIGS. 3-5 into the needle driver of FIGS. 6a-b.

FIG. 7a illustrates the insertion of the needle cartridge 14 into the tattoo machine drive unit 12 (cf. FIG. 2). For reasons of clarity, the only portion of the drive unit 12 that is illustrated in FIG. 7a is the needle driver 38. In the position of FIG. 7a, the south pole of the needle assembly magnet 44 faces the south pole of the drive magnet 46, and the needle cartridge 14 is inserted against the magnetic repulsion force between the needle assembly magnet 44 and the drive magnet 46. As the cartridge 14 is moved upwards, the needle assembly magnet 44 is maintained retracted in the retain position by the ferromagnetic washer 56 until the needle assembly magnet 44 has reached its equilibrium position at the centre of the drive magnet 46. As soon as the needle assembly magnet 44 has reached said equilibrium position, the strength of the magnetic engagement between the needle assembly magnet 44 and the drive magnet 46 will exceed the strength of the magnetic engagement between the needle assembly magnet 44 and the ferromagnetic washer 56. Thereafter, as the cartridge 14 is pressed deeper into the needle driver 38, the needle driver 38 will pull the needle assembly magnet 44 free from the ferromagnetic washer 56, bringing the needle driver 38 and the needle assembly 28 to the advanced position illustrated in FIG. 7b. The needle assembly magnet 44 is released from the ferromagnetic washer 56 when the downwards axial pulling force exerted by the drive magnet 46 upon the needle assembly magnet 44 exceeds a limit force determined by the strength of the magnetic engagement between the needle assembly magnet 44 and the ferromagnetic washer 56. After having reached the position of FIG. 7b, the cartridge 14 can be twisted in the socket 32 (cf. FIG. 2), thereby locking the bayonet wings 52a-b (cf. FIG. 3) of the cartridge 14 to the drive unit housing 34 (cf. FIG. 2).

Figure 7B:
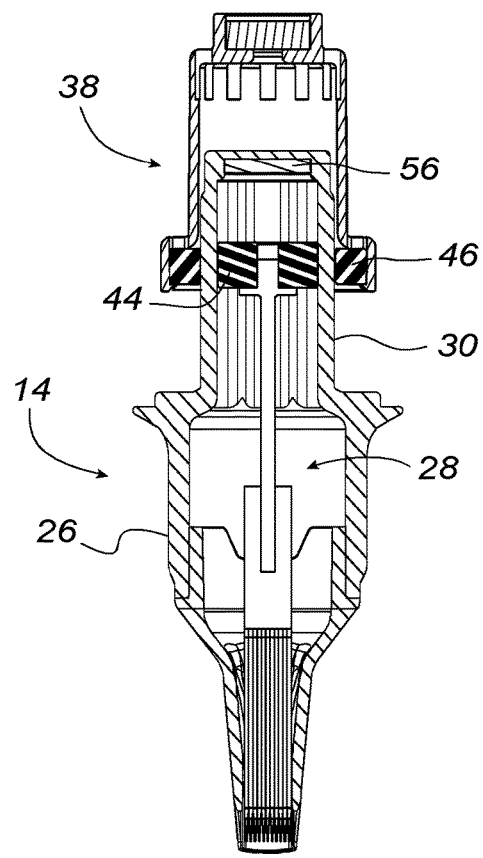
FIG. 7b is a longitudinal section illustrating the disposable tattoo needle cartridge of FIGS. 3-5 after having been inserted into the needle driver of FIGS. 6a-b and reached an initial position.
Figure 7C:
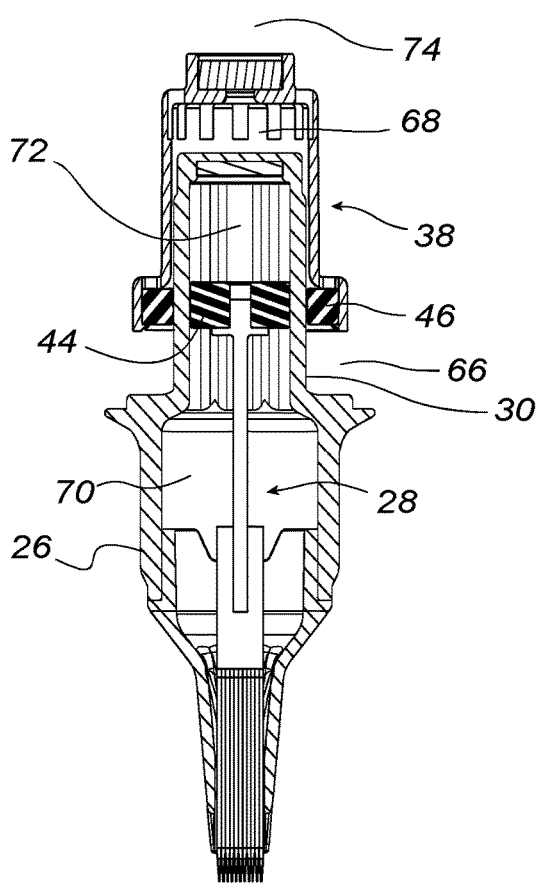
FIG. 7c is a longitudinal section illustrating the disposable tattoo needle cartridge of FIGS. 3-5 and the needle driver of FIGS. 6a-b during operation of the tattoo machine.

FIG. 7b illustrates the needle driver 38 and the needle assembly 28 in the advanced, relatively to the retain position of FIG. 7a, operating position when the cartridge 14 is properly connected to the drive unit 12 (cf. FIG. 2). In particular, FIG. 7b illustrates the needle assembly 28 at an initial, rearmost endpoint of an advanced operating position, at which endpoint the piston 24 (cf. FIG. 2) is at its retractedmost position, and the needles 16 do not protrude from the nozzle 18. At the operating position, the needle assembly magnet 44 is essentially free from the magnetic attraction of the ferromagnetic washer 56, such that the needle assembly 28 is freely slidable along the reciprocation axis in a non-resilient manner. As long as it is maintained in the advanced operating position, the needle assembly 28 is free to reciprocate without engaging with the ferromagnetic washer 56. As the needle driver 38 is reciprocated by the piston 24 along the reciprocation axis A (FIG. 2), the needle driver 38 and the needle assembly 28 will oscillate between the operating position end points respectively illustrated in FIGS. 7b and 7c.

To facilitate free motion, the external ridges 54 (cf. FIG. 3) of the rear end portion 30 of the needle cartridge housing 26 maintain an air gap between the drive magnet 46 and the outer surface of the rear end portion 30 of the needle cartridge housing 26. This air gap serves for allowing air to pass relatively freely between the space 66 (FIG. 7c) in front of the drive magnet 46 and the space 68 behind the drive magnet 46 when the drive magnet 46 moves at high speed.

Similarly, the internal ridges 62 (cf. FIG. 5) of the rear end portion 30 of the needle cartridge housing 26 maintain an air gap between the needle assembly magnet 44 and the inner surface of the rear end portion 30 of the needle cartridge housing 26. This air gap serves for allowing air to pass relatively freely between the space 70 (FIG. 7c) in front of the needle assembly magnet 44 and the space 72 behind the needle assembly magnet 44 when the needle assembly 28 moves at high speed.

The external ridges 65 (cf. FIG. 6a) of the needle driver 38 maintain an air gap between the needle driver 38 and the inner surface of the outer housing 34 (cf. FIG. 2) of the drive unit 12 (cf. FIG. 2). This air gap serves for allowing air to pass relatively freely between the space 66 (FIG. 7c) in front of the needle driver 38 and a space 74 behind the needle driver 38 when the needle driver 38 moves at high speed. The ridges 54, 62, 65 also serve for reducing friction and guiding the respective components along their axial motion. The air holes 64 (FIG. 6a-b) allow air to pass relatively freely between the space 68 (FIG. 7c) inside the cup-shaped needle driver 38 and the space 74 behind the needle driver 38 as the needle driver 38 moves at high speed. The ferromagnetic washer 56 will automatically re-engage with the needle assembly magnet 44 upon removal of the cartridge 14 from the drive unit 12. After twisting to release the bayonet joint, the cartridge 14 can be pulled out from the needle driver 38, such that the drive magnet 46 will pull back the needle assembly magnet 44 to its retracted retain position, where it will again engage with the ferromagnetic washer 56. Once the rearwards motion of the needle assembly magnet 44 has been stopped by the rigid back wall portion 27, a continued removal of the cartridge 14 from the needle driver 38 will release the engagement between the drive magnet 46 and the needle assembly magnet 44. Clearly, the retaining arrangement formed by the needle assembly magnet 44 and the ferromagnetic washer 56 allows re-engagement and re-release an indefinite amount of times. Thereby, the tattoo artist can safely remove and re-install the cartridge an unlimited number of times, and each time the needles 16 will be safely retracted and retained. This makes it easier for a tattoo artist to more frequently switch between needle types/cartridge types.

The strength of the needle assembly magnet 44 and the drive magnet 46, as well as the radial distance between the two, and the dimensions and material of the ferromagnetic washer 56 and the width of the gap 57 (FIG. 4), are preferably selected to satisfy the relation $$R_{44\text{-}46} < A_{44\text{-}56} < A_{44\text{-}46}$$

wherein $R_{44\text{-}46}$ is the axial component of the maximum repulsive force between the needle assembly magnet 44 and the drive magnet 46 as the cartridge 14 is gradually inserted into the drive unit 12;

$A_{44\text{-}56}$ is the axial component of the attraction force between the needle assembly magnet 44 and the ferromagnetic washer 56 when the needle assembly magnet 44 is in the retractedmost retain position; and $A_{44\text{-}46}$ is the axial component of the maximum returning force between the needle assembly magnet 44 and the drive magnet 46 if the needle assembly magnet 44 is gradually moved upwards from its equilibrium position inside the drive magnet 46.

Moreover, the drive magnet 50 of the piston 24, the driven magnet 48 of the needle driver 38, and any gap between them, are preferably selected to satisfy the relation $$A_{44\text{-}46} < A_{48\text{-}50}$$

wherein $A_{48\text{-}50}$ is the axial component of the attraction force between the drive magnet 50 of the piston 24 and the driven magnet 48 of the needle driver 38. This prevents the needle driver 38 from being pulled out of the drive unit 12 when the cartridge 14 is removed.

Thanks to the needle driver 38 being attached to the piston 24 only via the magnetic engagement between magnets 48, 50 (FIG. 2), the user can easily and quickly switch between needle drivers having different magnetic properties of their respective drive magnets 46, such that different levels of resilience may be obtained in the engagement between the drive magnet 46 and the needle assembly magnet 44. Expressed differently, it is possible to easily change the "give" of the tattoo machine, for a softer or harder run, by changing the needle driver. The yielding engagement between the drive magnet 46 and the needle assembly magnet 44 also protects the base unit 12 from damage in case the needles 16 strike an impenetrable object.

The drive magnet 46 is preferably of at least grade N48, and more preferably of at least grade N52. The needle assembly magnet 46 is also preferably of at least grade N48, and more preferably of at least grade N52.

The width, i.e., in the exemplary, circular symmetrical geometry of the illustrated embodiment, the diameter, of the needle assembly magnet 44 as measured in the radial direction, preferably exceeds its height as measured along the reciprocation axis A (FIG. 2). More particularly, the width of the needle assembly magnet 44 is preferably at least 1.5 times its height. Preferred approximate dimensions are a height of about 2 mm-4 mm, and more preferably about 2.5 mm-3.5 mm; and a diameter of about 5 mm-9 mm, and more preferably about 6 mm-8 mm.

The width of the drive magnet 46, as measured in the radial direction, preferably exceeds its height as measured along the reciprocation axis A (FIG. 2). More particularly, the width of the drive magnet 46 is preferably at least twice its height, and more preferably, at least three times its height.

Preferred approximate dimensions are a height of about 1.5 mm-3.5 mm, and more preferably about 2 mm-3 mm; and an inner diameter of about 7 mm-12 mm, and more preferably about 8 mm-11 mm.

A preferred radial distance between the needle assembly magnet 44 and the drive magnet 46 is about 0.5 mm-2.0 mm, and more preferably about 1.0 mm-1.5 mm. Preferably, the ridges 54, 62 have a height, as measured in the radial direction, of at least 0.25 mm.

A lower height of the magnets provides a more well-defined and distinct position of equilibrium in the positional relationship between the needle assembly magnet 44 and the drive magnet 46 at the expense of the strength of engagement between the two.

The invention has mainly been described above with reference to a few embodiments. However, as is readily appreciated by a person skilled in the art, other embodiments than the ones disclosed above are equally possible within the scope of the invention, as defined by the appended patent claims.

For example, a needle assembly retainer of magnetic type, involving a magnet 44 and a ferromagnetic washer 56, has been described (FIG. 4). Clearly, also other types of retaining arrangements can be used, such as a friction engagement between the magnet 44 and a tapering rearmost cross-section of the rear end housing portion 30. In fact, no retainer is needed at all within the cartridge. When inserting the cartridge 14 in the drive unit 12, the needle can be prevented from being pushed out of the cartridge using e.g. a suitable tool held at, or inserted through, the needle cartridge nozzle 18. The ferromagnetic washer need not be a washer; it can have any shape. It can be a non-magnetically polar component made of e.g. steel, or be a permanent magnet with a magnetic moment of its own. The term washer is intended to cover any sheet metal disc or chip, which need not be provided with a through-hole.

The magnets as well as the rear end portion 30 of the cartridge housing 26 have been illustrated to have a circular cross-section. This is not necessary; the cross-section of those components may be given any suitable shape allowing the needle assembly magnet 44 and the drive magnet 46 to engage in the radial direction.

A rigid back wall portion of the cartridge housing has been described to define a rearward stop position of the needle assembly 28. However, such a stop position may be provided by any other suitable structure, or not at all.

The needle driver 38 has been illustrated as a separate component, or at least as a component separable from the rest of the drive unit 12 (cf. FIGS. 6a-6b). This is not necessary; the very details on how a drive magnet is brought in axial reciprocation are irrelevant to the function of the cartridge 14 as such.

The invention claimed is:

1. A disposable tattoo needle cartridge for connecting to a tattoo machine drive unit, the tattoo needle cartridge comprising:
a cartridge housing;
a needle assembly comprising a needle driver connector and at least one needle, the needle driver connector being connectable to a needle driver of the tattoo machine drive unit for receiving a reciprocating motion, the needle assembly being slidingly arranged in the tattoo needle cartridge to allow the reciprocating motion along a reciprocation axis,
wherein the cartridge housing has a front end portion provided with a needle nozzle for allowing the at least one needle to reciprocatingly protrude from the tattoo needle cartridge, and a rear end portion configured to be connected to the tattoo machine drive unit, the tattoo needle cartridge being characterized in that the needle driver connector comprises a needle assembly magnet for connecting to a mating drive magnet of the needle driver in a contact-less manner in a radial, with respect to the reciprocation axis, connection direction; and
a releasable needle assembly retainer for retaining the needle assembly at a retracted retain position in which the at least one needle does not protrude from the needle nozzle,
wherein the needle assembly upon release of the needle assembly retainer is movable from the retracted retain position to an advanced operating position at which the at least one needle is free to reciprocate without engaging with the needle assembly retainer.

2. The disposable tattoo needle cartridge according to claim 1, wherein the needle assembly retainer is self-contained in the tattoo needle cartridge.

3. The disposable tattoo needle cartridge according to claim 1, wherein the needle assembly retainer is configured to automatically release when a force acting upon the needle assembly towards the needle nozzle exceeds a limit force.

4. The disposable tattoo needle cartridge according to claim 1, wherein the needle assembly retainer is configured to automatically engage with the needle assembly when the needle assembly reaches a retracted retain position.

5. The disposable tattoo needle cartridge according to claim 1, wherein the needle assembly retainer comprises a ferromagnetic element for holding the needle assembly magnet in the retracted position.

6. The disposable tattoo needle cartridge according to claim 1, the needle assembly magnet having a magnetic moment aligned in a first direction essentially parallel with the reciprocation axis.

7. The disposable tattoo needle cartridge according to claim 1, wherein the rear end portion of the cartridge housing is provided with at least one inner spacer element, introducing a radial gap between the needle assembly magnet and an inner wall surface of the rear end portion of the cartridge housing, for defining an air escape passage between a rear space behind the needle assembly magnet and a front space in front of the needle assembly magnet.

8. The disposable tattoo needle cartridge according to claim 1, wherein the rear end portion of the cartridge housing is provided with at least one outer spacer element for introducing a radial gap between an outer wall surface of the rear end portion of the cartridge housing and the drive magnet.

9. The disposable tattoo needle cartridge according to claim 1, wherein the rear end portion of the cartridge housing is sealed by a rigid wall.

10. The disposable tattoo needle cartridge according to claim 1, wherein the needle assembly is freely slidable along the reciprocation axis in a non-resilient manner.

11. The disposable tattoo needle cartridge according to claim 1, wherein a rear end of the needle driver connector comprises a radially extending ferromagnetic flange and a needle assembly magnet alignment structure extending rearwards from the ferromagnetic flange.

* * * * *